(12) United States Patent
Auld et al.

(10) Patent No.: US 9,066,678 B2
(45) Date of Patent: Jun. 30, 2015

(54) OPHTHALMIC ENDOILLUMINATORS WITH DIRECTED LIGHT

(75) Inventors: Jack R. Auld, Laguna Niguel, CA (US); Michael M. Martin, Newport Beach, CA (US); Michael J. Papac, Tustin, CA (US); Ronald T. Smith, Irvine, CA (US); Michael J. Yadlowsky, Sunnyvale, CA (US)

(73) Assignee: ALCON RESEARCH, LTD., Fort Worth, TX (US)

( * ) Notice: Subject to any disclaimer, the term of this patent is extended or adjusted under 35 U.S.C. 154(b) by 261 days.

(21) Appl. No.: 13/241,427

(22) Filed: Sep. 23, 2011

(65) Prior Publication Data

US 2013/0079598 A1 Mar. 28, 2013

(51) Int. Cl.
| | |
|---|---|
| *A61B 1/06* | (2006.01) |
| *A61B 1/07* | (2006.01) |
| *A61B 19/00* | (2006.01) |
| *A61B 3/00* | (2006.01) |
| *A61B 1/00* | (2006.01) |

(52) U.S. Cl.
CPC ............... *A61B 1/07* (2013.01); *A61B 19/5202* (2013.01); *A61B 2019/5206* (2013.01); *A61B 3/0008* (2013.01); *A61B 1/00183* (2013.01)

(58) Field of Classification Search
CPC ...... A61B 1/06; A61B 1/0607; A61B 1/0615; A61B 1/0623; A61B 1/0661; A61B 1/0676; A61B 1/07
USPC ........................ 600/249; 606/15; 385/115–133
See application file for complete search history.

(56) References Cited

U.S. PATENT DOCUMENTS

| | | | |
|---|---|---|---|
| 4,418,688 A | 12/1983 | Loeb | |
| 4,551,129 A * | 11/1985 | Coleman et al. ................ | 604/21 |
| 5,045,397 A | 9/1991 | Jensen | |
| 5,112,328 A | 5/1992 | Taboada et al. | |
| 5,396,571 A | 3/1995 | Saadatmanesh et al. | |
| 5,514,125 A | 5/1996 | Lasser et al. | |
| 5,916,149 A * | 6/1999 | Ryan, Jr. ....................... | 600/177 |
| 5,953,477 A | 9/1999 | Wach et al. | |
| 6,144,791 A | 11/2000 | Wach et al. | |
| 6,428,553 B1 | 8/2002 | Trese | |
| 6,575,989 B1 | 6/2003 | Scheller et al. | |
| 6,802,838 B2 | 10/2004 | Loeb et al. | |
| 6,893,432 B2 | 5/2005 | Intintoli et al. | |
| 6,984,230 B2 | 1/2006 | Scheller et al. | |

(Continued)

FOREIGN PATENT DOCUMENTS

| | | |
|---|---|---|
| EP | 0305170 A2 | 3/1989 |
| WO | 2009/009246 A1 | 1/2009 |

OTHER PUBLICATIONS

PCT/EP2012/54366; Written Opinion of the International Searching Authority, Nov. 13, 2012, 6 pgs.

*Primary Examiner* — Jerry Cumberledge
*Assistant Examiner* — Tessa Matthews
(74) *Attorney, Agent, or Firm* — Jason Finch

(57) ABSTRACT

Certain embodiments of an endoilluminator may include a cannula, an intermediate material, and an optical fiber. The cannula has a substantially cylindrical shape that defines an interior region and has a cylindrical axis. The intermediate material is disposed within the interior region. The optical fiber is disposed within the intermediate material and has a fiber optical axis and a distal end configured to emit light. The emitted light has an illumination pattern with an illumination axis that is not parallel to the cylindrical axis.

8 Claims, 5 Drawing Sheets

(56) References Cited

U.S. PATENT DOCUMENTS

| | | |
|---|---|---|
| 7,285,107 B1 | 10/2007 | Charles |
| 7,306,588 B2 * | 12/2007 | Loeb et al. ............... 606/15 |
| 7,566,173 B2 | 7/2009 | Auld et al. |
| 7,740,733 B2 | 6/2010 | Takafumi |
| 7,783,346 B2 * | 8/2010 | Smith et al. ............... 604/21 |
| 2003/0088257 A1 | 5/2003 | Awh et al. |
| 2003/0199860 A1 | 10/2003 | Loeb et al. |
| 2007/0005093 A1 * | 1/2007 | Cox ............... 606/198 |
| 2007/0179430 A1 | 8/2007 | Smith et al. |
| 2007/0265602 A1 | 11/2007 | Mordaunt et al. |
| 2008/0051770 A1 | 2/2008 | Scheller et al. |
| 2008/0319463 A1 * | 12/2008 | Hickingbotham ............ 606/161 |
| 2009/0287197 A1 * | 11/2009 | Hanley et al. ............... 606/15 |
| 2010/0114147 A1 * | 5/2010 | Biyani ............... 606/191 |
| 2010/0125172 A1 | 5/2010 | Jayaraj |
| 2011/0112377 A1 * | 5/2011 | Papac et al. ............... 600/249 |
| 2015/0005751 A1 * | 1/2015 | Neuberger et al. ............ 606/3 |

* cited by examiner

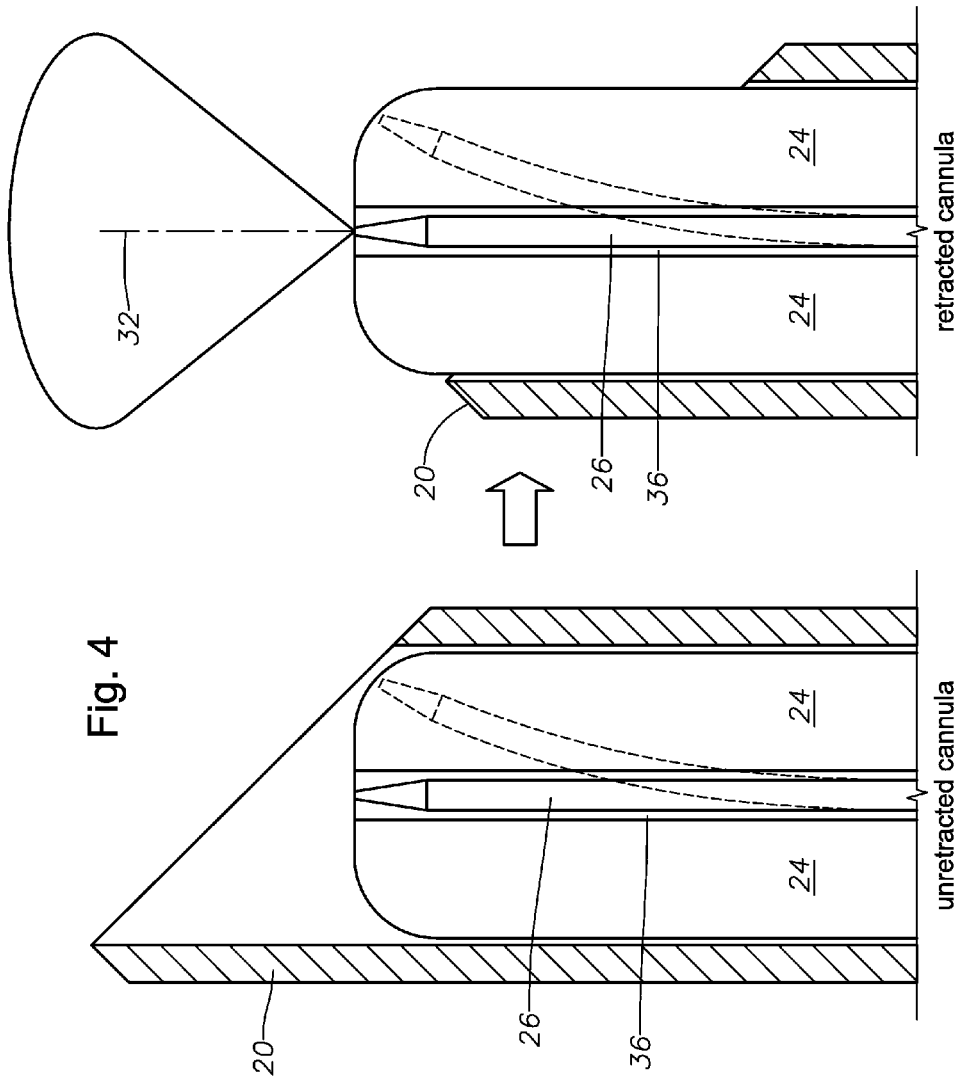

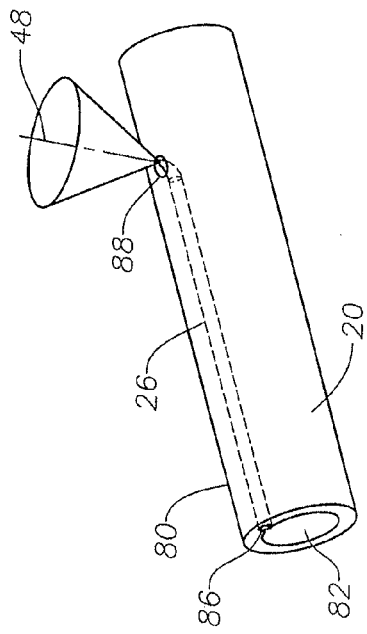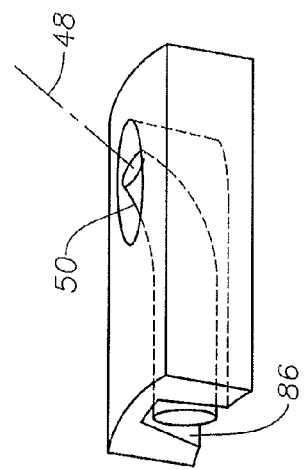
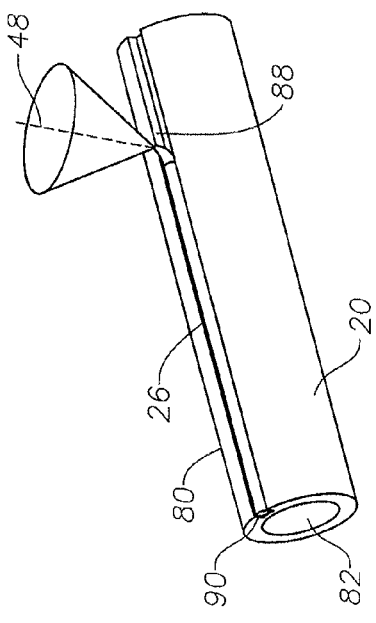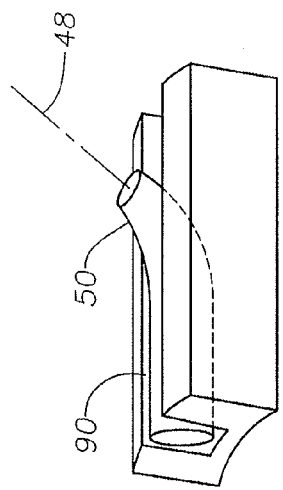
Fig. 5A
Fig. 5B

US 9,066,678 B2

OPHTHALMIC ENDOILLUMINATORS WITH DIRECTED LIGHT

TECHNICAL FIELD

The present disclosure relates generally to surgical instruments, and more particularly to ophthalmic endoilluminators with directed light.

BACKGROUND

Endoilluminators typically have a cannula filled with one or more optical fibers that emit light. Certain endoilluminators may direct light in a particular manner. For example, the optical fibers may be bent to direct light in a particular direction. As another example, the optical fibers may be shaped to direct light within a range of angles. These endoilluminators, however, may not be able to direct light in a suitable fashion in certain situations.

BRIEF SUMMARY

The description describes different embodiments of systems that may be used to direct light. For example, certain embodiments may include a cannula, an intermediate material, and an optical fiber. The cannula has a substantially cylindrical shape that defines an interior region and has a cylindrical axis. The intermediate material is disposed within the interior region. The optical fiber is disposed within the intermediate material and has a fiber optical axis and a distal end configured to emit light. The emitted light has an illumination pattern with an illumination axis that is not parallel to the cylindrical axis.

As another example, certain embodiments may include a cannula and an optical fiber. The cannula has a substantially cylindrical shape with a cylindrical axis, and has an outer surface and an inner surface defining an interior region. The optical fiber is coupled to the cannula and has a fiber optical axis and a shaped distal end configured to emit light. The emitted light has an illumination pattern with an illumination axis that is not parallel to the cylindrical axis.

As yet another example, certain embodiments may include a cannula, an intermediate material, and an optical fiber. The cannula has a substantially cylindrical shape defining an interior region, and the cylindrical shape has a cylindrical axis. The intermediate material is disposed within the interior region and defines a fiber pathway. The optical fiber is disposed within the fiber pathway, and has a fiber optical axis and a distal end configured to emit light with an illumination pattern having an illumination axis. At least a portion of the fiber optical axis proximal the distal end is not parallel to the cylindrical axis, and the illumination axis is not parallel to the cylindrical axis.

BRIEF DESCRIPTION OF THE DRAWINGS

Exemplary embodiments of the present disclosure are described by way of example in greater detail with reference to the figures, in which:

FIG. 4 illustrates an example of an endoilluminator with a retractable cannula according to certain embodiments; and FIGS. 5A and 5B illustrate examples of endoilluminators with an optical fiber coupled to the cannula according to certain embodiments.

DETAILED DESCRIPTION OF CERTAIN EMBODIMENTS

Figure 1:
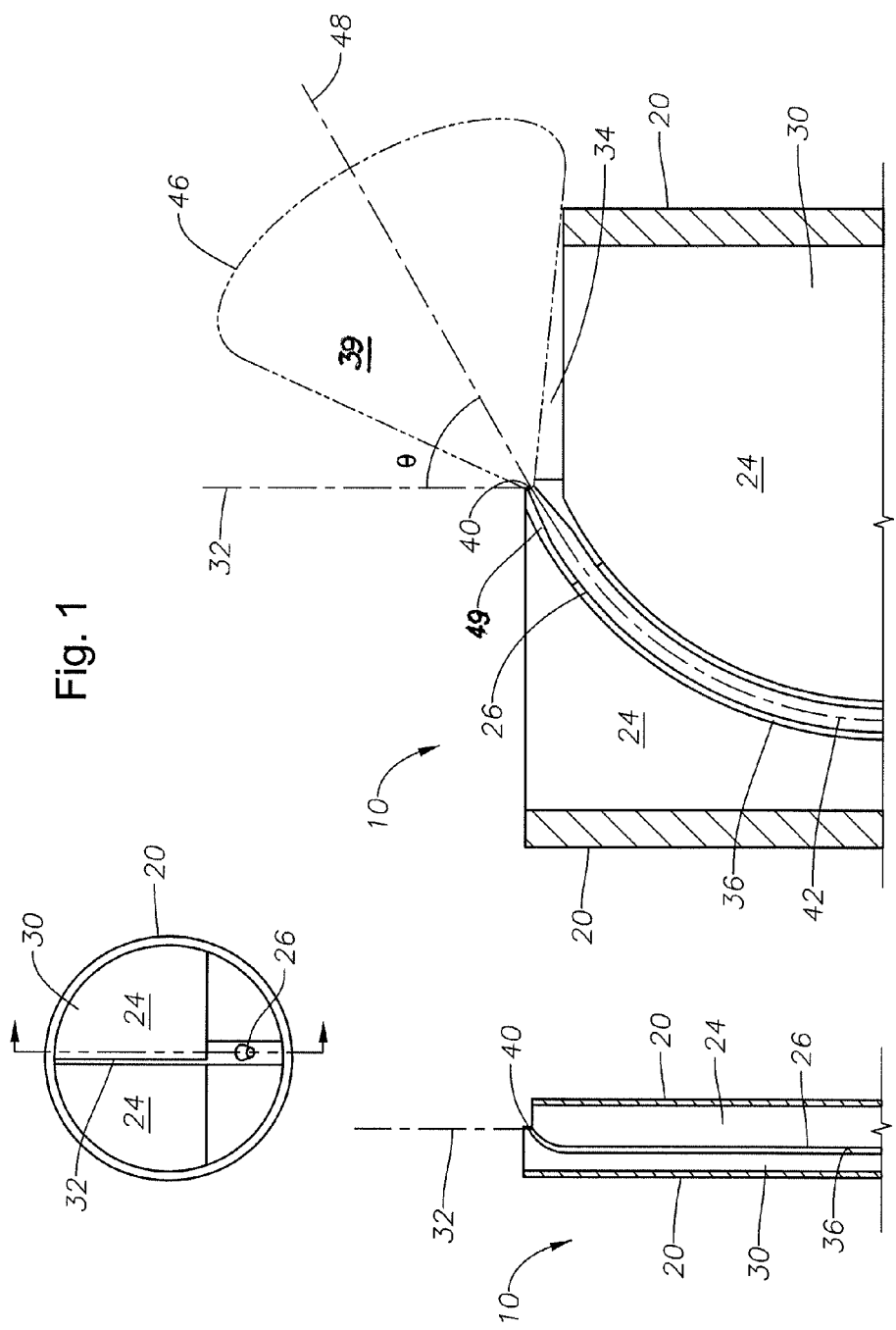
FIG. 1 illustrates an example of an endoilluminator according to certain embodiments.

Certain embodiments may be directed to an endoillumination probe that has an optical fiber (such as a small diameter optical fiber) that emits light. The fiber may be configured to direct the illumination pattern of the emitted light in a particular manner. For example, the fiber may be bent or have an asymmetrically-shaped distal end to direct the light at an angle to the cylindrical axis of the probe. As another example, the distal end may be shaped to increase the divergence angle of the light beyond that which results from a distal end with a flat end normal to the fiber axis.

Referring now to the description and drawings, example embodiments of the disclosed apparatuses, systems, and methods are shown in detail. The description and drawings are not intended to be exhaustive or otherwise limit or restrict the claims to the specific embodiments shown in the drawings and disclosed in the description. Although the drawings represent possible embodiments, the drawings are not necessarily to scale and certain features may be exaggerated, removed, or partially sectioned to better illustrate the embodiments.

FIG. 1 illustrates an example of an endoilluminator according to certain embodiments. In certain embodiments, system 10 may be inserted into a human (or other living or previously living) body for medical purposes, such as for ophthalmic surgery. For example, system 10 may be an endoilluminator surgical instrument for projecting light into an interior of an eyeball. In the illustrated example, system 10 includes a cannula 20, an intermediate material 24, and an optical fiber 26.

Cannula 20 may have any suitable shape and size. In certain embodiments, cannula 20 has a substantially cylindrical shape that defines an interior region 30. The cylindrical shape has a cylindrical axis 32 and any suitable height and diameter, such as a height in the range of 25 to 50 millimeters (mm) and a diameter in the range of 1 mm or less. Cannula 20 may comprise any suitable material, e.g., a metal such as stainless steel. In certain embodiments, cannula 20 may have sharp edges that can make incisions in material such as body tissue.

In certain embodiments, intermediate material 24 is disposed within interior region 30. Intermediate material 24 may be any suitable material that can provide structural support for optical fiber 26. Examples of intermediate material 24 include material with a Young's modulus that is larger than that of stainless steel, such as tungsten, molybdenum, tungsten carbide, tungsten rhenium.

Intermediate material 24 defines a fiber pathway 36 within which optical fiber 26 is disposed. Fiber pathway 36 may be shaped to allow optical fiber 26 to direct light in a particular direction as optical fiber 26 protrudes from fiber pathway 36. In the illustrated example, fiber pathway 36 is curved so optical fiber 26 directs light at an angle θ from axis 32 as optical fiber 26 protrudes from fiber pathway 36. Angle θ may have any suitable value, such as a value in any of the following ranges: less than 30, 30 to 60, 60 to 90, or 90 to 120 degrees.

In certain embodiments, cannula 20 and/or intermediate material 24 may be shaped to avoid the emitted light. In the example, a relief 34 may be shaped into cannula 20 and/or intermediate material 24 to allow cannula 20 and/or intermediate material 24 to avoid vignetting, or blocking, emitted light.

In certain embodiments, optical fiber 26 is disposed within intermediate material 24. Optical fiber 26 is a fiber comprising a transparent material (e.g., glass or plastic) that operates as a waveguide to transmit light from a proximal end (not shown) to a distal end 40. The light may originate at a laser source. Optical fiber 26 has a transparent fiber core surrounded by a cladding material. The core has an optical axis 42 that defines the path along which light propagates, which is typically along the center of the fiber core. Optical fiber 26 may have any suitable core diameter, for example, less than 100 micrometers (μm), such as 50 to 60 μm.

The light 39 emitted by optical fiber 26 has an illumination pattern 46 with an illumination axis 48 that is centered within illumination pattern 46. In certain embodiments, optical fiber 26 is shaped by fiber pathway 36 to yield illumination pattern 46 with illumination axis 48 that is not parallel to the cylindrical axis 32. For example, at least a portion of fiber optical axis 42 proximate distal end 40 is not parallel to cylindrical axis 32, such that the emitted light has illumination axis 48 that is not parallel to cylindrical axis 32. "Proximate distal end 40" may include the region at and near distal end 40, such as within less than 10, 5, or 2 centimeters (cm) of distal end 40.

In certain embodiments, distal end 40 may be shaped to direct the emitted light in a particular manner. Distal end 40 may be shaped to spread light to angles greater than the numerical aperture of optical fiber 26, e.g., angles up to and greater than 90 or 120 degrees. For example, distal end 40 may have a compound parabolic concentrator (CPC) or tapered shape. A tapered shape may be a truncated or cone shape. Distal end 40 may be shaped to direct light in a particular direction. In the illustrated example, distal end 40 is symmetric to maintain optical axis 42 of optical fiber 26. In other examples, distal end 40 may be asymmetric to change optical axis 42 of optical fiber 26.

A shaped end may utilize internal reflection to spatially concentrate light within fiber 26 up to the end to yield higher angular divergence as the light exits the end. An encapsulant material 49 surrounding the end may operate as a cladding material to guide the light to the end. (Encapsulant material 49 may be disposed outwardly from distal end 40 and proximate distal end 40.) Encapsulant material 49 may be any suitable material, such as an adhesive, with any suitable refractive index, such as a low refractive index of less than 2.0, e.g., approximately 1.3 to 1.4. Examples of encapsulant material 49 include products available from NORLAND, MASTER BOND, DYMAX, and MYPOLYMER.

Figure 2:
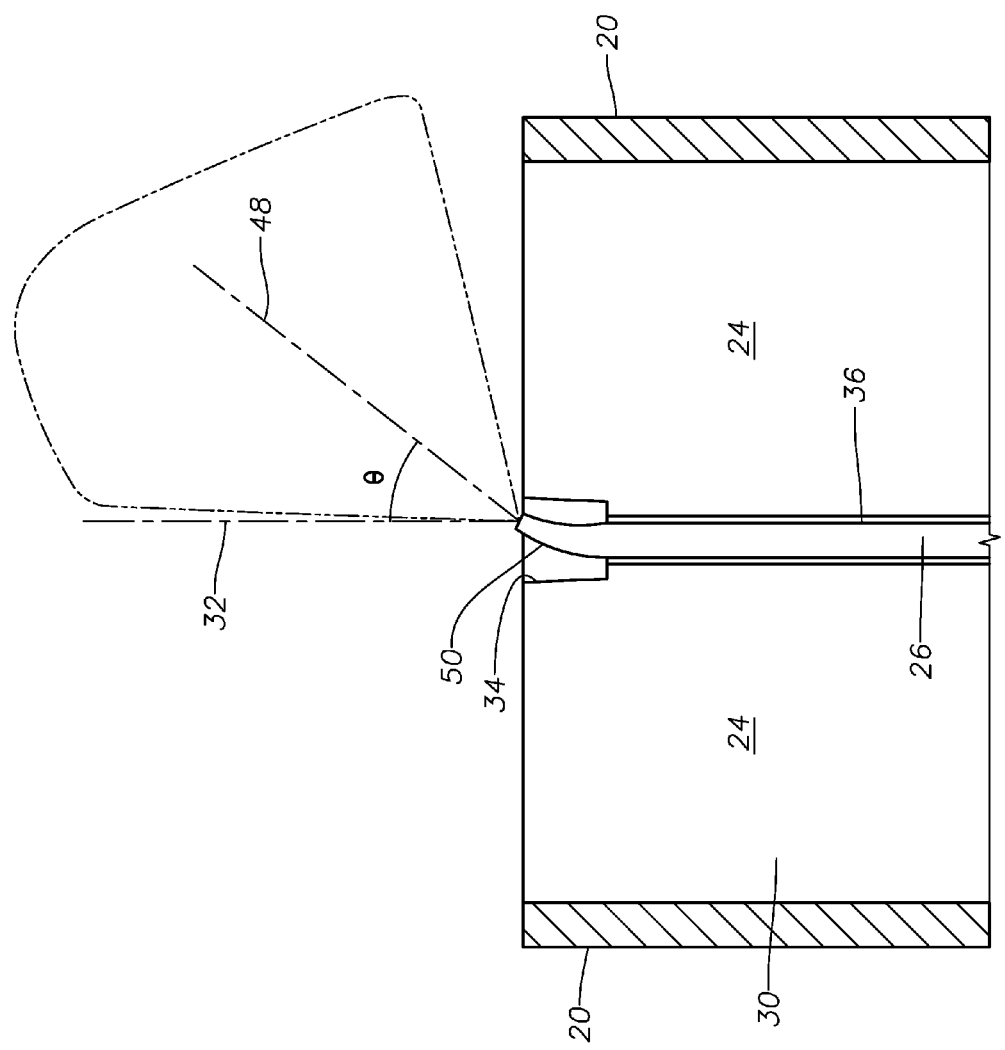
FIG. 2 illustrates another example of an endoilluminator according to certain embodiments.

FIG. 2 illustrates another example of an endoilluminator according to certain embodiments. In the illustrated example, fiber pathway 36 is parallel to cylindrical axis 32, but illumination axis 48 is not parallel to axis 32. In certain embodiments, optical fiber 26 has a shaped distal end 50 with an asymmetric taper that changes optical axis 42 of optical fiber 26. In the illustrated example, shaped distal end 50 bends optical axis 42 to an angular bias of angle θ with respect to axis 32.

In certain embodiments, cannula 20 and/or intermediate material 24 may be shaped to avoid the emitted light. In the example, a counterbore relief 34 may be shaped into intermediate material 24 to allow intermediate material 24 to avoid vignetting, or blocking, emitted light.

Figure 3:
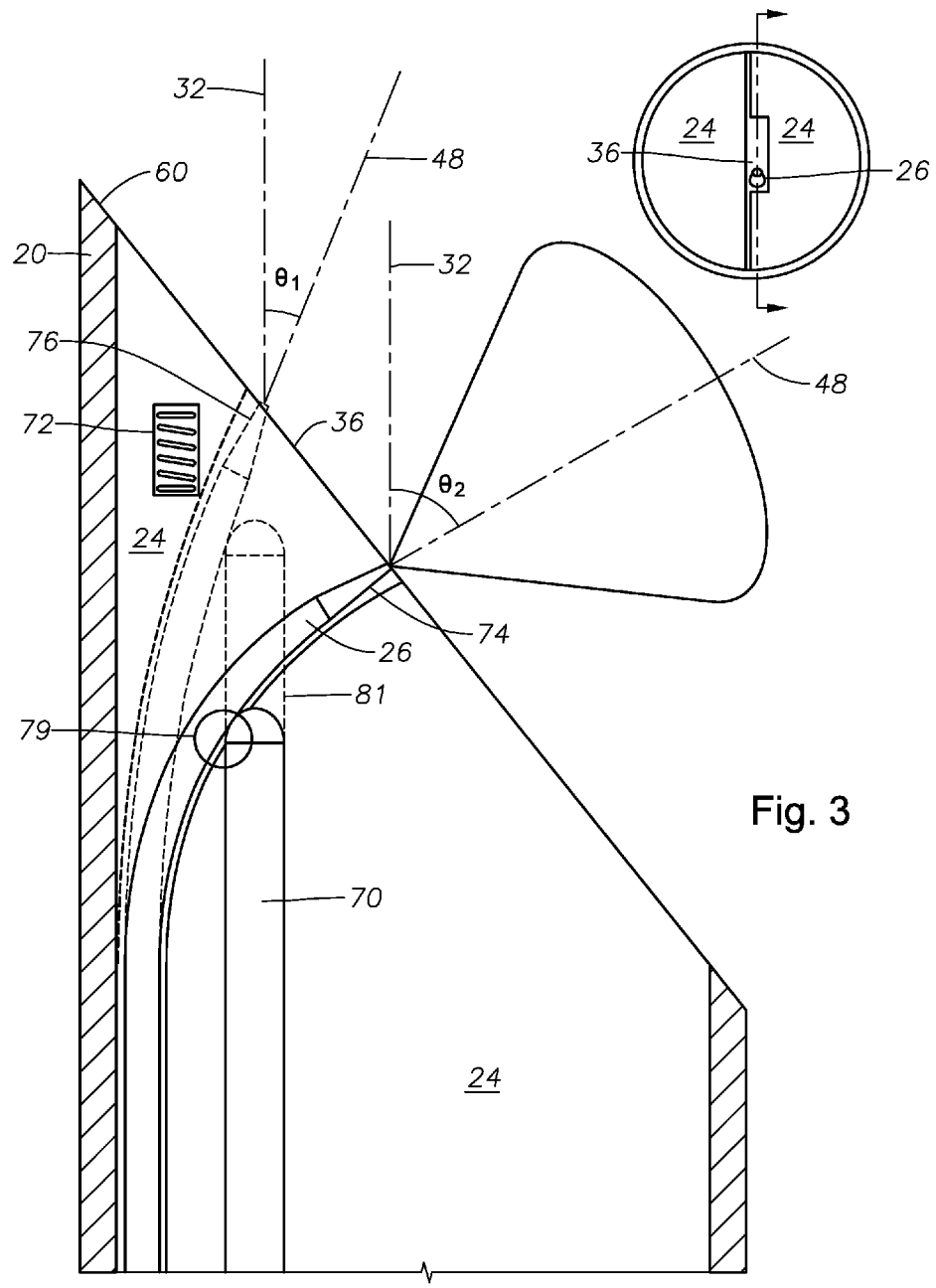
FIG. 3 illustrates an example of an endoilluminator with an actuator according to certain embodiments.

FIG. 3 illustrates an example of an endoilluminator with an actuator 70 according to certain embodiments. In certain embodiments, system 10 may include actuator 70 disposed within interior region 30. Actuator 70 may move optical fiber 26 from a first position 74 to a second position 76 to change an angle between illumination axis 48 and cylindrical axis 32 from a first value $θ_1$ to a second value $θ_2$. Actuator 70 may comprise any suitable mechanism. In certain embodiments, actuator 70 may include a rod or wire that can be moved using movement mechanisms in response to, for example, user input. Movement mechanisms may include any suitable devices that can move an object, such as mechanical and/or electrical devices, for example, springs, gears, electric motors, piezoelectric devices, and a handheld actuated lever on the device hand piece.

Any suitable approach may be used to return optical fiber 26 to first position 74. In certain embodiments, a return mechanism 72 may return optical fiber 26 to first position 74. Return mechanism 72 may include movement mechanisms such as a spring that can move optical fiber 26. In other embodiments, optical fiber 26 may be shaped to return first position 74. For example, optical fiber 26 may move to second position 76 when actuator 70 applies force to optical fiber 26, but may then return first position 74 when the force is removed. In certain examples, optical fiber 26 may be baked into a curved configuration that returns to first position 74.

In yet other embodiments, optical fiber 26 may be mechanically coupled by a coupling 79 to actuator 70 to allow actuator 70 to return to first position 74. For example, coupling 79 may move optical fiber 26 to second position 76 when actuator 70 moves to a second position, but may return optical fiber 26 to first position 74 when actuator 70 returns to first position 74. Coupling 79 may include any suitable approach for joining objects, for example, adhesive material, connecting elements (such as notches for hooks) formed in one or more of the objects, or a coupling element that couples the objects.

In certain embodiments, interior material 24 may be shaped to form an actuator pathway 81 that allows for the movement of actuator 70. In certain embodiments, fiber pathway 36 may be shaped to accommodate the movement of optical fiber 26. In the example, fiber pathway 36 has a larger opening that allows optical fiber 26 to move from first position 74 to second position 76 back to first position 74.

In certain embodiments, a distal end 60 of cannula 20 may be configured to perform incisions. For example, distal end 60 may have sharp edges that can cut through skin and other body tissue.

FIG. 4 illustrates an example of an endoilluminator with a retractable cannula 20 according to certain embodiments. In certain embodiments, cannula 20 may retract such that distal end 40 of optical fiber 26 protrudes more than distal end 60 of cannula 20. In the illustrated example, cannula 20 may be an incising cannula 20 and may be retraced to allow blunt intermediate material 24 to protrude. Angled illumination may be provided any suitable manner. In the example, illumination may be provided by an actuator 70 as described with reference to FIG. 3.

FIGS. 5A and 5B illustrate examples of endoilluminators with optical fiber 26 coupled to cannula 20 according to certain embodiments. Optical fiber 26 may be coupled to cannula 20 in any suitable manner, such as with an adhesive. Examples of adhesives include cyanacryolates and epoxies. In the illustrated example, cannula 20 has an outer surface 80 and an inner surface 82 that defines interior region 30.

FIG. 5A illustrates an example of an endoilluminator with inner surface 82 that forms an inner channel 86. Inner channel 86 may have a width and depth that is approximately the diameter of optical fiber 26. Optical fiber may be disposed at least partially or even mostly or all within inner channel 86. An adhesive and/or encapsulant (adhesive/ encapsulant) material 88 may secure optical fiber 26 to inner channel 86. Material 88 may have any suitable optical index, such as less than 2.0, for example, 1.3 to 1.4. Examples of material 88 may be similar to the examples of encapsulant material 49. In addition, in these embodiments, an adhesive may be augmented by using a ultra thin (e.g., less than 10 micrometer (μm) in thickness) polymer heat shrink tube, a thin piece of adhesive tape, or a vapor deposited coating to strengthen the attachment of the fiber to the cannula.

FIG. 5B illustrates an example of an endoilluminator with outer surface 80 that forms an outer channel 90. Outer channel 90 may have a width and depth that is approximately the diameter of optical fiber 26. Optical fiber may be disposed at least partially or even mostly or all within outer channel 90. An adhesive/encapsulant material 88 may secure optical fiber 26 to outer channel 90.

In certain embodiments, optical fiber 26 may be disposed outwardly from outer surface 80, where outer surface 80 does not have outer channel 90 and may be substantially flat where optical fiber 26 is in contact with outer surface 80. In these embodiments, optical fiber 26 may be coupled outwardly from outer surface 80 using adhesive/encapsulant material 88.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, and the operations of the systems and apparatuses may be performed by more, fewer, or other components. As another example, modifications may be made to the methods disclosed herein. The methods may include more, fewer, or other steps, and the steps may be performed in any suitable order.

Other modifications are possible without departing from the scope of the invention. For example, the description illustrates embodiments in particular practical applications, yet other applications will be apparent to those skilled in the art. In addition, future developments will occur in the arts discussed herein, and the disclosed systems, apparatuses, and methods will be utilized with such future developments.

The scope of the invention should not be determined with reference to the description. In accordance with patent statutes, the description explains and illustrates the principles and modes of operation of the invention using exemplary embodiments. The description enables others skilled in the art to utilize the systems, apparatuses, and methods in various embodiments and with various modifications, but should not be used to determine the scope of the invention.

The scope of the invention should be determined with reference to the claims and the full scope of equivalents to which the claims are entitled. All claims terms should be given their broadest reasonable constructions and their ordinary meanings as understood by those skilled in the art, unless an explicit indication to the contrary is made herein. For example, use of the singular articles such as "a," "the," etc. should be read to recite one or more of the indicated elements, unless a claim recites an explicit limitation to the contrary. As another example, "each" refers to each member of a set or each member of a subset of a set, where a set may include zero, one, or more than one element. In sum, the invention is capable of modification, and the scope of the invention should be determined, not with reference to the description, but with reference to the claims and their full scope of equivalents.

What is claimed is:

1. A system comprising:
   a cannula having a substantially cylindrical shape defining an interior region and an opening at a distal most end of the cannula, the cylindrical shape having a cylindrical axis;
   an intermediate material disposed within the interior region, the intermediate material defining a fixed fiber pathway having a portion that is curved with respect to the cylindrical axis, the fixed fiber pathway being wider towards the opening at the distal most end of the cannula;
   an optical fiber disposed within the fixed fiber pathway, the optical fiber having a fiber optical axis and a distal end configured to emit light with an illumination pattern having an illumination axis, at least a portion of the fiber optical axis proximate the distal end not parallel to the cylindrical axis, the illumination axis not parallel to the cylindrical axis; and
   an actuator disposed within the intermediate material, the actuator comprising a rod configured to move the distal end of the optical fiber from a first position within the fixed fiber pathway to a second position within the fixed fiber pathway to change an angle between the illumination axis and the cylindrical axis from a first value to a second value.

2. The system of claim 1, further comprising a return mechanism configured to return the optical fiber to the first position.

3. The system of claim 1, the optical fiber shaped to return to the first position.

4. The system of claim 1, the optical fiber mechanically coupled to the actuator to allow the actuator to return the optical fiber to the first position.

5. The system of claim 1, a distal end of the cannula configured to make incisions.

6. The system of claim 1, the cannula configured to retract such that the distal end of the optical fiber protrudes more than a distal end of the cannula.

7. The system of claim 1, the intermediate material shaped to avoid the emitted light.

8. The system of claim 1, the cannula shaped to avoid the emitted light.

* * * * *